(12) United States Patent
Hein et al.

(10) Patent No.: US 10,869,612 B2
(45) Date of Patent: Dec. 22, 2020

(54) TRANSDUCER WITH MAGNETIC NANOWIRE ARRAY

(71) Applicants: Boston Scientific Scimed Inc., Maple Grove, MN (US); Regents of the University of Minnesota, Minneapolis, MN (US)

(72) Inventors: Matthew Hein, Eden Prairie, MN (US); Daniel J. Foster, Lino Lakes, MN (US); David R. Wulfman, Minneapolis, MN (US); Bethanie J. H. Stadler, Shoreview, MN (US)

(73) Assignees: Boston Scientific Scimed Inc., Maple Grove, MN (US); Regents of the University of Minnesota, Minneapolis, MN (US)

( * ) Notice: Subject to any disclaimer, the term of this patent is extended or adjusted under 35 U.S.C. 154(b) by 760 days.

(21) Appl. No.: 15/396,682

(22) Filed: Jan. 1, 2017

(65) Prior Publication Data
US 2017/0188881 A1 Jul. 6, 2017

Related U.S. Application Data

(60) Provisional application No. 62/274,349, filed on Jan. 3, 2016.

(51) Int. Cl.
*A61B 5/00* (2006.01)
*A61B 5/06* (2006.01)
(Continued)

(52) U.S. Cl.
CPC ............ *A61B 5/062* (2013.01); *A61B 5/6852* (2013.01); *A61B 34/20* (2016.02);
(Continued)

(58) Field of Classification Search
CPC . A61B 5/062; A61B 34/20; A61B 2562/0223; G01R 33/0011
See application file for complete search history.

(56) References Cited

U.S. PATENT DOCUMENTS 6,404,192 B1 * 6/2002 Chiesi ................... G01R 33/04
324/253
9,112,364 B2 8/2015 Partovi
(Continued)

FOREIGN PATENT DOCUMENTS

WO 2003014757 A1 2/2003

OTHER PUBLICATIONS

Fischer, Gregory A. and Edelstein, Alan S. "Macro-Magnetic Modeling of the ARL Microelectromechanical System (MEMS) Flux Concentrator." Army Research Laboratory, ARL-TR-5778, Sep. 2011, 24 pages.
(Continued)

*Primary Examiner* — Eric D. Bertram
(74) *Attorney, Agent, or Firm* — Faegre Drinker Biddle & Reath LLP

(57) ABSTRACT

A transducer includes a planar coil coupled to a magnetic flux guide. The magnetic flux guide includes an array of nanowires. The transducer could include a plurality of magnetic flux guides and a plurality of planar coils stacked together. The flux guides and planar coils could alternative in the stacked configuration.

20 Claims, 6 Drawing Sheets

(51) Int. Cl.
*G01R 33/04* (2006.01)
*G01R 33/00* (2006.01)
*A61B 34/20* (2016.01)

(52) U.S. Cl.
CPC .......... G01R 33/0011 (2013.01); G01R 33/04 (2013.01); *A61B 2034/2051* (2016.02); *A61B 2562/0223* (2013.01)

(56) References Cited

U.S. PATENT DOCUMENTS

| | | | |
|---|---|---|---|
| 9,139,905 B2 | 9/2015 | Elam et al. | |
| 2012/0019241 A1* | 1/2012 | Patak | H01F 1/15391 324/244 |
| 2013/0099334 A1* | 4/2013 | Mohan | G01R 33/04 257/421 |
| 2013/0231657 A1* | 9/2013 | Datta | A61B 18/1492 606/41 |

OTHER PUBLICATIONS

Singh, Ashutosh K and Mandal, Kalyan. "Effect of Aspect Ratio and Temperature on Magnetic Properties of Permalloy Nanowires." Journal of Nanoscience and Nanotechnology, 14(7):5036-5041, 2014.
International Search Report and Written Opinion issued in PCT/US2017/012002, dated May 11, 2017, 16 pages.

* cited by examiner

TRANSDUCER WITH MAGNETIC NANOWIRE ARRAY

CROSS-REFERENCE TO RELATED APPLICATION

This application claims priority to Provisional Application No. 62/274,349, filed Jan. 3, 2016, which is herein incorporated by reference in its entirety.

TECHNICAL FIELD

The present invention relates to devices and methods involving compact transducers.

BACKGROUND

Transducers can be used to convert one form of energy to another form. For example, magnetic transducers can convert a sensed magnetic field into an electrical signal, and piezoelectric transducers can convert force into an electrical signal.

SUMMARY

In Example 1, a transducer includes a planar coil coupled to a magnetic flux guide having an array of nanowires.

In Example 2, the transducer of Example 1, further including a plurality of magnetic flux guides and a plurality of planar coils, wherein the plurality of magnetic flux guides and planar coils alternate in a stacked configuration.

In Example 3, the transducer of Example 2, wherein some of the plurality of planar coils are configured to receive an excitation signal and wherein the other of the plurality of planar coils are configured to sense magnetic fields.

In Example 4, the transducer of any of Examples 1-3, wherein the planar coil is embedded in the array of nanowires.

In Example 5, the transducer of any of Examples 1-4, further including a plurality of planar coils, wherein a first planar coil is positioned on one side of the magnetic flux guide and wherein a second planar coil is positioned on an opposite side of the magnetic flux guide.

In Example 6, the transducer of Example 1, further including a magnetic sensor coupled with the magnetic flux guide and planar coil.

In Example 7, the transducer of Example 6, wherein the magnetic sensor is positioned on a first side of the magnetic flux guide, and wherein the planar coil is positioned on an opposite side of the magnetic flux guide as the magnetic sensor.

In Example 8, the transducer of any of Examples 1-3, further including a plurality of planar coils each sandwiched between layers of oxide material to form first and second assemblies, wherein the magnetic flux guide is sandwiched between the first and second assemblies.

In Example 9, the transducer of any of Examples 1-8, wherein the magnetic flux guide includes a template comprising one of anodized aluminum, titanium oxide, or a polymer.

In Example 10, the transducer of any of Examples 1-9, wherein the array of nanowires comprise a high permeability ferromagnetic metal.

In Example 11, wherein the nanowires in the array of nanowires are multilayered.

In Example 12, the transducer of any of Examples 1-11, wherein the array of nanowires comprise at least one of nickel-iron, cobalt, and nickel.

In Example 13, the transducer of any of Examples 1-12, wherein the flux guide has a height of 1-300 microns.

In Example 14, the transducer of any of Examples 1-13, wherein the individual nanowires have an aspect ratio of at least 5.

In Example 15, a catheter housing the transducer of any of Examples 1-14.

In Example 16, a minimally-invasive medical device comprising includes a body housing a transducer configured to sense magnetic fields. The transducer includes a planar coil coupled with a flux guide that includes an array of nanowires.

In Example 17, the minimally-invasive medical device of Example 16, further including a plurality of magnetic flux guides and a plurality of planar coils. The plurality of magnetic flux guides and planar coils alternate in a stacked configuration.

In Example 18, the minimally-invasive medical device of Example 17, wherein some of the plurality of planar coils are configured to receive an excitation signal and wherein the other of the plurality of planar coils are configured to sense magnetic fields.

In Example 19, the minimally-invasive medical device of any of Examples 16-18, wherein the planar coil is embedded in the array of nanowires.

In Example 20, the minimally-invasive medical device of Example 16, further including a plurality of planar coils, wherein a first planar coil is positioned on one side of the magnetic flux guide and wherein a second planar coil is positioned on an opposite side of the magnetic flux guide.

In Example 21, the minimally-invasive medical device of Example 16, further including a magnetic sensor coupled with the magnetic flux guide and planar coil.

In Example 22, the minimally-invasive medical device of Example 21, wherein the magnetic sensor includes a magnetoresistive element.

In Example 23, the minimally-invasive medical device of any of Examples 21-22, wherein the magnetic sensor is positioned on a first side of the magnetic flux guide, and wherein the planar coil is positioned on an opposite side of the magnetic flux guide as the magnetic sensor.

In Example 24, the minimally-invasive medical device of Example 16, further including a plurality of planar coils each sandwiched between layers of oxide material to form first and second assemblies. The magnetic flux guide is sandwiched between the first and second assemblies.

In Example 25, the minimally-invasive medical device of any of Examples 16-24, wherein the magnetic flux guide includes a template comprising one of anodized aluminum, titanium oxide, or a polymer.

In Example 26, the minimally-invasive medical device of any of Examples 16-25, wherein the array of nanowires includes a high permeability ferromagnetic metal.

In Example 27, the minimally-invasive medical device of any of Examples 16-26, wherein the array of nanowires includes nickel-iron.

In Example 28, the minimally-invasive medical device of any of Examples 16-27, further including a plurality of transducers positioned within the minimally-invasive medical device.

In Example 29, the minimally-invasive medical device of any of Examples 16-28, wherein the individual nanowires have an aspect ratio of at least 5.

In Example 30, a catheter includes a flux guide including an array of nanowires, a first planar coil positioned adjacent a first side of the flux guide, and a second planer coil positioned adjacent a second side of the flux guide opposite the first side.

In Example 31, the catheter of Example 30, wherein the flux guide is disc shaped.

In Example 32, the catheter of any of Examples 30-31, wherein the flux guide includes an anodized aluminum or titanium oxide template.

In Example 33, the catheter of any of Examples 30-32, wherein the flux guide forms a center aperture.

In Example 34, the catheter of any of Examples 30-33, wherein the first and second planar coils are coupled together by a coil link that extends through the flux guide.

In Example 35, the catheter of any of Examples 30-34, wherein the first and second planar coils are each sandwiched between or embedded in layers of oxide or a polymer.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
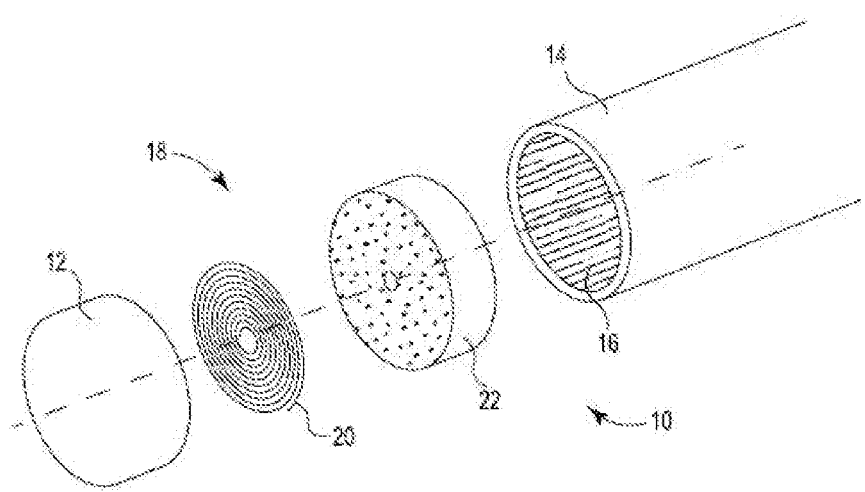
FIG. 1 shows a partial exploded view of a top portion of a medical device and a transducer, in accordance with certain embodiments of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Transducers can be used to convert one form of energy to another form. For example, magnetic transducers can convert a sensed magnetic field into an electrical signal. Magnetic transducers can include elements like coils and sensors that convert sensed magnetic fields into an electrical signal, or vice versa. The effectiveness of coiled magnetic transducers, for example, can depend on a number of parameters including the number of coils, number of coil turns, coil volume, and coil thickness among others. The ability to modify these parameters can be constrained when the available space for housing a magnetic transducer is limited. Moreover, fitting multiple transducers or types of transducers within a device with limited space can be challenging. Features of the present disclosure are accordingly directed to compact transducer designs that utilize a flux guide.

FIG. 1 shows a partial exploded view of an end of a medical device 10 like a catheter, which may feature a diameter ranging from about 300 um to 20 mm. The medical device 10 includes a top 12 and body 14 that form a central aperture 16 where the medical device 10 may house a transducer 18. The transducer 18 includes at least one planar coil 20 and flux guide 22. The planar coil 20 includes windings that are wound or formed and positioned within a plane. The coil 20 is configured to sense magnetic fields/flux and convert the sensed magnetic fields/flux to an electrical signal. The flux guide 22 directs magnetic fields towards the planar coil 20—essentially amplifying the magnetic fields directed to the planar coil 20. In embodiments, the flux guide 22 can direct magnetic fields towards multiple planar coils adjacent to the flux guide. The flux guide 22 includes an array or sheet of nanowires that guide magnetic fields along an elongated direction of the nanowires. The flux guide 22 is oriented such that the elongated direction of the nanowires is aligned with a direction normal to the planar coil 20. Each nanowire is configured to have a high aspect ratio resulting in an array that can be characterized as having high uniaxially-shape anisotropic properties in the elongated direction.

Figure 2:
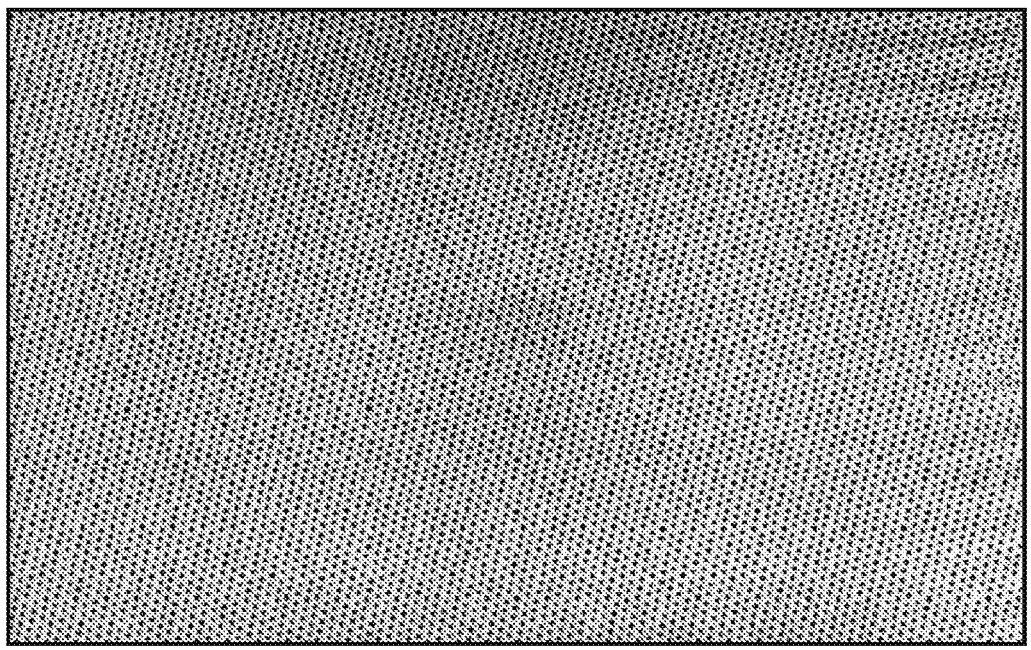
FIG. 2 shows a partial top view of a nanowire template, in accordance with certain embodiments of the present disclosure.

The array of nanowires can be created using a template, shown in FIG. 2, such as one made of anodized aluminum oxide (AAO) or anodized titanium oxides. In the process of anodizing, certain oxides form nanopores, like those shown in FIG. 2, in which nanowires can be plated into using techniques like electrodeposition, chemical vapor deposition, and atomic layer deposition. The pores can have pore diameters ranging from about 3 nm to 200 nm, lengths ranging from about 1 nm to 300 um, and inter-pore spacing ranging from about 5 nm to 300 nm—although Applicants appreciate other dimensions can be used. The nanowires can form within the pores. In some embodiments, a template can be formed from a variety of polymers like polyethylene terephthalate (PET), polycarbonate, or other polymers arranged to provide deposition of high-aspect ratio structures.

Figure 3:
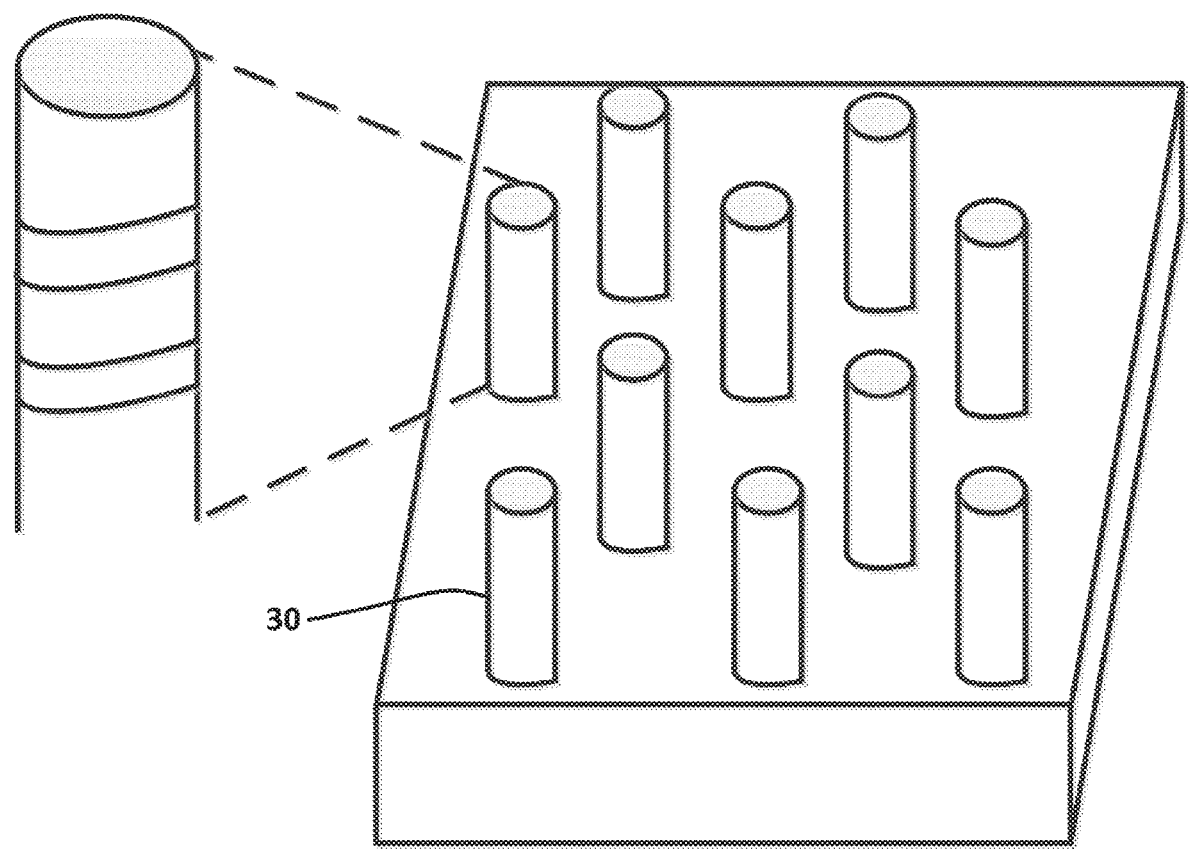
FIG. 3 shows a perspective, schematic view of an array of nanowires, in accordance with certain embodiments of the present disclosure.

FIG. 3 shows a schematic of an array of nanowires 30. Although not shown in FIG. 3, the nanowires 30 may be positioned within a template as described above. Magnetic properties of the nanowires, and therefore flux guide, depend on a variety of parameters including length, diameter, wire-to-wire spacing, material layering, and material composition of the nanowires and respective layers. Nanowires can be made of high permeability ferromagnetic metals like metals comprising nickel iron. As shown in FIG. 3 nanowires can be multilayered. For example, nanowires may include alternating layers of cobalt and nickel iron, etc. In embodiments, a multilayered nanowire may include alternating layers of 10 nm cobalt and 100 nm nickel.

Nanowires of the present disclosure may be dimensioned to feature a high aspect ratio (e.g., length/diameter). An aspect ratio of a nanowire influences an effect known as magnetic shape anisotropy, which affects the direction of magnetization for a given shape and material. For example, a cylindrically-shaped magnet material like a nanowire contemplated by the present disclosure has a shape anisotropy in an axial direction that increases as an aspect ratio of the nanowire increases. A high magnetic shape anisotropy along a nanowire's axis encourages permeability along the axis. As such, a flux guide including a sheet or array of nanowires can direct an increased magnetic field towards a coil or sensor. Flux guides therefore can provide compact geometry while also providing anisotropy that is more directionally selective than anisotropy provided by non-nanowire planar flux guides. For example, a flux guide's geometry could be isotropic or planar (e.g., thickness/diameter=1/10=100 um/1 mm, 1 mm/1 cm) and the nanowires could still provide out-of-plane directionality due to the high aspect ratio of the nanowire of which be 10,000 (e.g., 100 um/10 nm). In other words, an aspect ratio of the flux guide (e.g, thickness/diameter) could be low—thin with relatively larger diameter—and still provide nanowires with a high aspect ratio effect.

In some embodiments, the template can act as a substrate on which coils, like copper coils, can be electroplated onto. Although no intervening layers are shown in FIG. 1, the planar coil and flux guide do not need to be directly coupled to function. For example, a substrate may be positioned between the flux guide and planar coil to assist with forming the coil on the flux guide.

The transducer design described above results in an effective yet compact transducer for sensing magnetic fields by coupling a planar coil with a nanowire flux guide. In embodiments, the planar coil could have a height of 0.50-500 microns and the flux guide could have a height of 0.10-500 microns. In some embodiments, the planar coil could have a height of 2-10 microns and the flux guide could have a height of 50-150 microns. A height of the flux guide may depend on diameters of nanopores (and therefore nanowires) used in the template. For example, a nanowire with 30 nm diameter with a goal aspect ratio of at least 5 would call for a nanowire length (and therefore flux guide height or thickness) of at least 150 nm.

Compact designs can allow for multiple transducers to be positioned in a variety of orientations in devices with tight size and space constraints. For example, a medical device like a catheter or guidewire may use multiple magnetic transducers each oriented along a different axis to sense magnetic fields along with different axis. Such a configuration may enable monitoring and tracking of a medical device in multiple dimensions while the medical device is being navigated in a person's body during medical procedures. The above- and below-described transducers may permit a transducer to be oriented such that a planar coil's normal direction is perpendicular to an elongated axis of a medical device—an orientation with tight space constraints.

Figure 4:
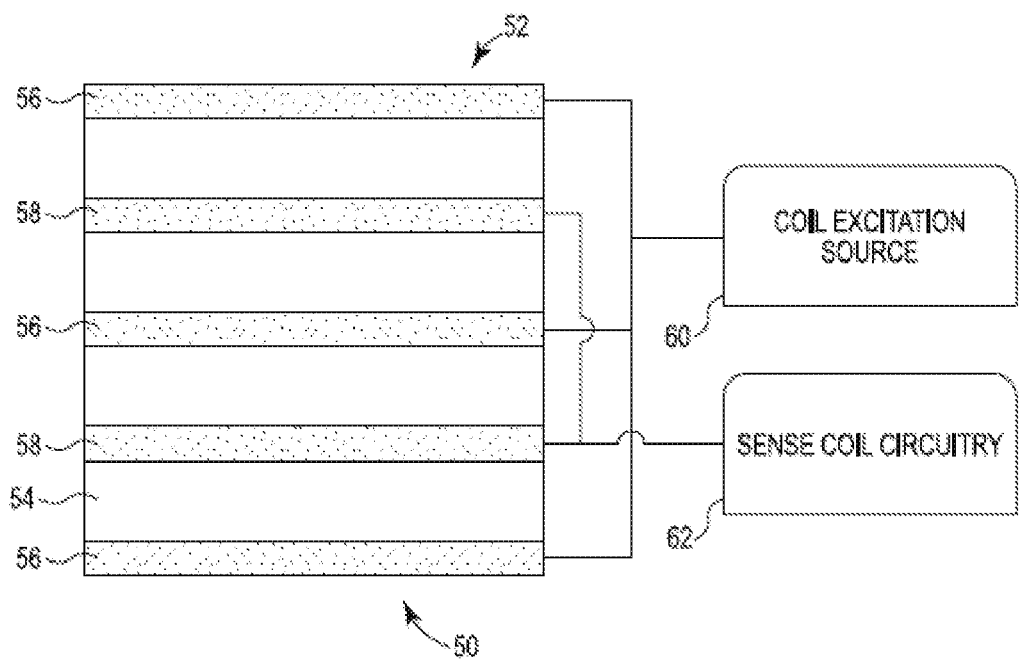
FIG. 4 shows side view of a transducer, in accordance with certain embodiments of the present disclosure.

FIG. 4 shows schematic of a transducer and optional circuitry for creating a fluxgate-like device. The transducer 50 includes coils 52 and flux guides 54 positioned adjacent to each other. The coils 52 and flux guides 54 are stacked in an alternating configuration. Using a plurality of both coils and flux guides can increase sensitivity of the transducer 50 and can provide the transducer 50 with sensing capabilities in multiple directions. Although the coils 52 and flux guides 54 are shown as being different layers, the coils can be embedded within the flux guide. For example, the coils can be deposited into the flux guide.

FIG. 4 also shows circuitry that turns certain coils 56 of the transducer into saturation coils while other coils 58 function as sensing coils. Saturation coils 56 are electrically coupled to an excitation source 60 that sends an excitation signal (e.g., sine wave, square wave) to the coils causing the coils to emit magnetic fields. Coils 58 sense both the emitted magnetic fields of saturation coils 56 and other magnetic fields, convert the sensed magnetic fields into an electrical signal, and send the electrical signal to sensing circuitry 62. This configuration acts as a fluxgate coupled with flux guides 54 positioned between coils to direct magnetic fields to the sensing coils 58.

In addition to the configurations shown and explained above, transducers could also include magnetic sensors such as magnetoresistive, Hall, and magneto-inductive sensors. For example, a nanowire flux guide could be sandwiched between a planar coil and a magnetic sensor. In this configuration, the coil would act as a biasing element within the transducer and the magnetic sensor would sense magnetic fields with assistance from the flux guide. Alternatively, the transducer could include just a magnetic sensor coupled with a nanowire flux guide. The nanowire flux guide in these configurations would function like the flux guides described in detail above.

Figure 5:
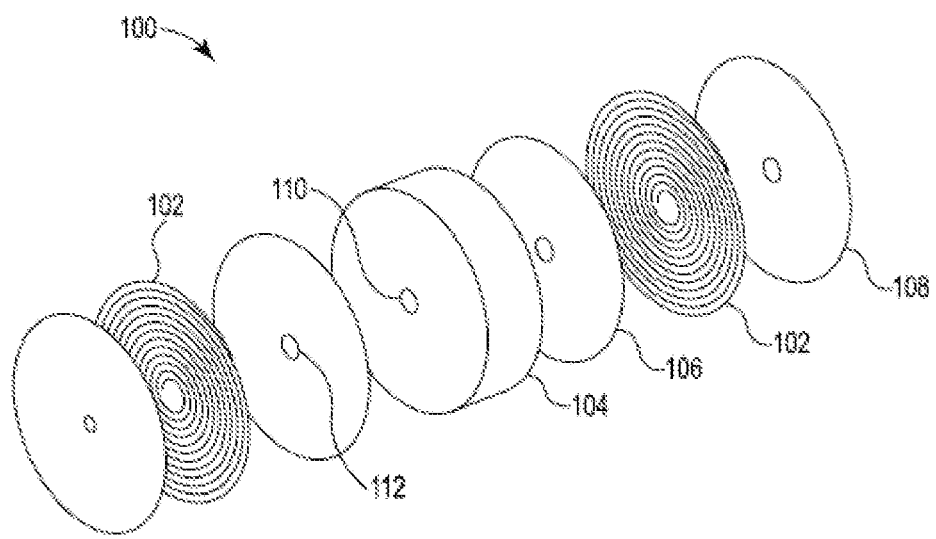
FIG. 5 shows a partial exploded view of a transducer, in accordance with certain embodiments of the present disclosure.

FIG. 5 shows an exploded view of a transducer 100 having multiple coils 102 and a nanowire flux guide 104. The coils 102 are covered by oxide layers formed around the coils such as layers 106 and 108. However, the coils 102 need not be completely covered by oxide layers. For example, a final winding at an outer diameter of the coil may be exposed to permit access for an electrical connector to be coupled to the coil. The oxide-covered coils are positioned on each side of the flux guide 104, which is shown in FIG. 5 as being disc shaped. The flux guide 104 forms a central aperture 110 that is aligned with an aperture 112 formed in adjacent oxide layers such that the transducer 100 has a central thru-hole. The thru-hole permits features like guide wires to pass through the transducer 100 when positioned within a medical device. The coils 102 can be electrically and physically coupled together with a linking wire or connector that passes through the flux guide 104. The transducer 100 may include multiple planar coils on either side of the flux guide 104.

Figure 6:
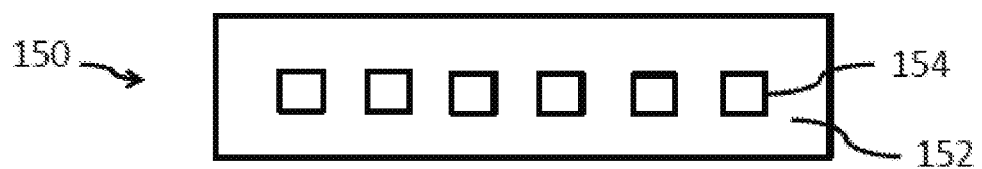
FIG. 6 shows a schematic section view of a transducer, in accordance with certain embodiments of the present disclosure.

FIG. 6 shows a schematic section view of a transducer 150 having a nanowire flux guide 152 with an embedded coil 154. As previously mentioned, nanowires can be created using a template such as one made of anodized aluminum oxide. In the embodiment shown in FIG. 6, the coil 154 is etched into an AAO template and includes multiple coils turns within a single plane. The coil 154 is configured to sense magnetic fields/flux and convert the sensed magnetic fields/flux to an electrical signal. The flux guide 152 directs magnetic fields towards the planar coil 154 to amplify the magnetic fields directed to the coil.

Figure 7:
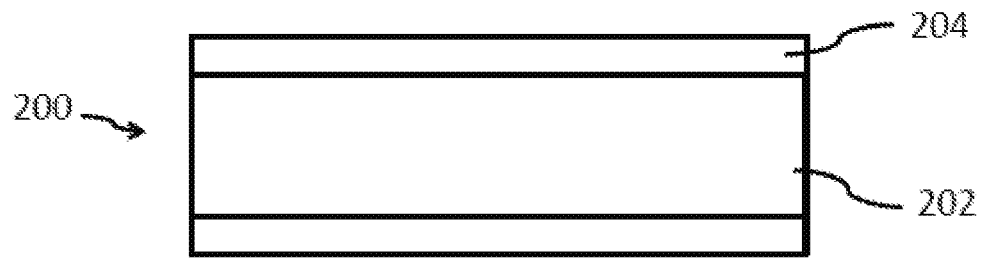
FIG. 7 shows a schematic side view of a transformer, in accordance with certain embodiments of the present disclosure.

FIG. 7 shows a schematic side view of a transformer 200 having a flux guide 202 with multiple coils 204. The top coil 204 can function as a primary coil and the bottom coil can function as a secondary coil. The flux guide 202 facilitates transfer of magnetic flux from the primary coil to the secondary coil. For example, varying current in the primary coil induces a varying electromotive force in the secondary coil via electromagnetic induction. The flux guide 202 acts to direct magnetic flux towards the secondary coil.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A minimally-invasive medical device comprising:
   a body housing a transducer configured to sense magnetic fields, wherein the transducer includes a first planar coil and a second planar coil both coupled with a first magnetic flux guide that includes an array of nanowires comprising a ferromagnetic metal, the first planar coil is positioned on one side of the first magnetic flux guide and the second planar coil is positioned on an opposite side of the first magnetic flux guide.

2. The minimally-invasive medical device of claim 1, further comprising:
   a plurality of magnetic flux guides, which includes the first magnetic flux guide, and a plurality of planar coils, which includes the first and second planar coils, wherein the plurality of magnetic flux guides and planar coils alternate in a stacked configuration.

3. The minimally-invasive medical device of claim 2, wherein some of the plurality of planar coils are configured to receive an excitation signal and wherein the other of the plurality of planar coils are configured to sense magnetic fields.

4. The minimally-invasive medical device of claim 1, wherein the first planar coil is embedded in the array of nanowires.

5. The minimally-invasive medical device of claim 1, further comprising:
   a magnetic sensor coupled with the first magnetic flux guide and the first planar coil.

6. The minimally-invasive medical device of claim 5, wherein the magnetic sensor includes a magnetoresistive element.

7. The minimally-invasive medical device of claim 6, wherein the magnetic sensor is positioned on a first side of the first magnetic flux guide, and wherein the first planar coil is positioned on an opposite side of the first magnetic flux guide as the magnetic sensor.

8. The minimally-invasive medical device of claim 1, further comprising:
   a plurality of planar coils, which include the first and second planar coils, each sandwiched between layers of oxide material to form first and second assemblies, wherein the first magnetic flux guide is sandwiched between the first and second assemblies.

9. The minimally-invasive medical device of claim 1, wherein the first magnetic flux guide includes a template comprising one of anodized aluminum, titanium oxide, or a polymer.

10. The minimally-invasive medical device of claim 1, wherein the array of nanowires comprises nickel-iron.

11. The minimally-invasive medical device of claim 1, further comprising:
    a plurality of transducers positioned within the minimally-invasive medical device.

12. The minimally-invasive medical device of claim 1, wherein the individual nanowires have an aspect ratio of at least 5.

13. The minimally-invasive medical device of claim 1, wherein nanowires have a diameter of 3-200 nm.

14. The minimally-invasive medical device of claim 1, wherein the body has a diameter of 300 um 20 mm.

15. The minimally-invasive medical device of claim 1, wherein the body is a catheter body.

16. The minimally-invasive medical device of claim 1, wherein the nanowires extend lengthwise along a direction perpendicular to a plane along which the first planar coil is coiled.

17. The minimally-invasive medical device of claim 16, wherein the nanowires have a shape anisotropy along the direction.

18. The minimally-invasive medical device of claim 1, wherein the nanowires are arranged to direct magnetic flux towards the first planar coil.

19. The minimally-invasive medical device of claim 1, wherein the body extends along a longitudinal axis, wherein the nanowires extend lengthwise along the longitudinal axis.

20. A minimally-invasive medical device comprising:
    a body housing a transducer configured to sense magnetic fields, wherein the transducer includes a planar coil coupled with a magnetic flux guide that includes an array of nanowires comprising a ferromagnetic metal, wherein the magnetic flux guide includes a template comprising one of anodized aluminum, titanium oxide, or a polymer.

* * * * *